(12) United States Patent
Bruederle

(10) Patent No.: US 9,697,726 B2
(45) Date of Patent: Jul. 4, 2017

(54) APPARATUS AND METHOD FOR DETECTING THE PRESENCE OF A MOBILE DEVICE

(71) Applicant: Karl Storz GmbH & Co. KG, Tuttlingen (DE)

(72) Inventor: Klaus Bruederle, Moos (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 14/738,023

(22) Filed: Jun. 12, 2015

(65) Prior Publication Data

US 2015/0364035 A1 Dec. 17, 2015

(30) Foreign Application Priority Data

Jun. 13, 2014 (DE) .................. 10 2014 108 364

(51) Int. Cl.
| | | |
|---|---|---|
| G05B 11/01 | (2006.01) |
| G08C 19/16 | (2006.01) |
| G08C 17/02 | (2006.01) |
| G01S 1/70 | (2006.01) |
| A61B 17/00 | (2006.01) |

(52) U.S. Cl.
CPC ............ *G08C 17/02* (2013.01); *G01S 1/70* (2013.01); *A61B 2017/00057* (2013.01); *A61B 2017/00212* (2013.01); *A61B 2017/00221* (2013.01); *A61B 2017/00367* (2013.01); *G08C 2201/50* (2013.01); *G08C 2201/91* (2013.01)

(58) Field of Classification Search
CPC ........ G08C 17/02; G08C 2201/91; G01S 1/70

USPC ................................................. 340/12.22
See application file for complete search history.

(56) References Cited

U.S. PATENT DOCUMENTS

| 4,385,354 A | 5/1983 | Hornfeld et al. |
|---|---|---|
| 2007/0150078 A1* | 6/2007 | Tanabe .................. G08C 17/00 700/33 |

(Continued)

FOREIGN PATENT DOCUMENTS

DE  102007059311 A1  6/2008

OTHER PUBLICATIONS

European Search Report Application No. EP15171039.9 Completed: Oct. 28, 2015;Mailing Date: Oct. 5, 2015 8 pages.

(Continued)

*Primary Examiner* — Tanmay Shah
(74) *Attorney, Agent, or Firm* — Whitmyer IP Group LLC

(57) ABSTRACT

Apparatus and method for detecting the presence of a mobile device in a room, the apparatus having a device control unit for controlling a target device, a mobile device for controlling a target device, a signal source for emitting a pilot signal, a signal receiver for receiving a room signal caused by the pilot signal, the signal receiver arranged in the vicinity of the mobile device and outputting a measurement signal in response to the room signal, a signal control unit for controlling the signal source, the signal control unit controlling the signal source based on an actual value signal obtained from the measurement signal in such a manner that the actual value signal approaches a predefinable target value signal over time, and the device control unit configured to control the target device by means of the mobile device on the basis of whether the approach has taken place.

19 Claims, 6 Drawing Sheets

(56) References Cited

U.S. PATENT DOCUMENTS

| | | |
|---|---|---|
| 2009/0080348 A1 | 3/2009 | Hamel et al. |
| 2011/0063429 A1 | 3/2011 | Contolini et al. |
| 2014/0153747 A1* | 6/2014 | Contolini ................ G06F 19/34 |
| | | 381/122 |

OTHER PUBLICATIONS

Jan Lunze: Regelungstechnik 1—Systemtheoretische Grundlagen, Analyse und Entwurf Einschleifiger Regelungen; 9. überarbeitete Auflage, Springer Vieweg, 63 pages.

* cited by examiner

APPARATUS AND METHOD FOR DETECTING THE PRESENCE OF A MOBILE DEVICE

CROSSREFERENCES TO RELATED APPLICATIONS

This application claims priority from German patent application DE 10 2014 108 364.4, filed on Jun. 13, 2014. The entire content of this priority application is incorporated herein by reference.

BACKGROUND

The disclosure relates to an apparatus and a method for detecting the presence of a mobile device in a room, in particular in a medical treatment room.

The starting situation is as follows: at least one mobile device and at least one target device which is intended to be controlled using the mobile device are situated in a room. The mobile device can be removed from the room during a conventional workflow. In particular, it is possible to easily move the mobile device to another room and to use it in the other room.

In contrast, the target device is intended to be understood as meaning the equipment in the room. Therefore, in the case of the target device, there is no provision for the target device to be removed from the room during a normal workflow. Therefore, the target devices include, in particular, those devices which are designed to permanently remain in the room.

In order to be able to control the target device using the mobile device, there is a device control unit for controlling the target device. The mobile device transmits control commands, in particular using wireless transmission, to the device control unit which then in turn controls the target device. In this case, the device control unit usually acts as a broker between the mobile device and the target device and verifies the control commands.

This set-up is found, for example, in an operating room where an operating table as the target device can be remotely controlled by means of a remote control as the mobile device via a wireless connection. In this case, it is important for the spatial relationship between the mobile device and the target device to be protected, i.e., the mobile device and the target device must be in the same room in order to ensure reliable operation. In this case, a criterion for reliable operation is often that the operator can directly discern effects of his inputs in the process behaviour.

Due to the usually wireless connection between the mobile device and the device control unit, it is no longer ensured, unlike in the case of wired connections, that the mobile device is in the same room as the target device just because a connection exists between the mobile device and the target device. In addition, a one-to-one assignment is generally not desired since the mobile device is intended to also be able to be used in other rooms, but not unintentionally.

Due to the wireless transmission technologies which are available nowadays, it is readily possible for the mobile device to be in another room, possibly even far away from the room in which the target device is situated. The situation may therefore arise in which a user outside the room inadvertently operates the target device. In particular, the situation may arise in which the user having the mobile device is situated in a first room in order to control a target device situated there, but the user actually, i.e., incorrectly, controls a target device in a second room. Such errors are particularly dangerous in medical treatment rooms, in particular, for example an operating room.

The prior art has already disclosed interesting aspects. For example, US 2011/0063429 describes that an ultrasound signal is emitted inside a room and an attempt is made to intercept the ultrasound signal with a control microphone which is used to control the target device. If the ultrasound signal can be detected by the control microphone, this allows the conclusion that the control microphone is in the correct room, i.e., in the room in which the ultrasound signal is emitted.

Another idea is to equip a mobile microphone for voice control with an RFID chip. If the identification number of the microphone is also received when all RFID chips in the room are queried, it can be concluded from this that the microphone is in the correct room, i.e., in the room in which the RFID query was carried out.

Despite the great reliability of the methods from the prior art, particular potential error situations may nevertheless possibly not be reliably detected. Therefore, an object is to show an improved apparatus and an improved method for detecting the presence of a mobile device in a room. In this case, the intention is also, in particular, to ensure in unusual and rare configurations that a mobile device is actually detected as being present in a room only when the mobile device is also actually present in this room.

SUMMARY

According to a first aspect, the object is achieved by means of an apparatus for detecting the presence of a mobile device in a room, the apparatus having
  a device control unit for controlling a target device,
  a mobile device for controlling a target device using the device control unit,
  a signal source for emitting a pilot signal,
  a signal receiver for receiving a room signal caused by the pilot signal, the signal receiver being arranged in the spatial vicinity of the mobile device and configured to output a measurement signal in response to the received room signal,
  a signal control unit for controlling the signal source,
  the signal control unit configured to control the signal source on the basis of an actual value signal obtained from the measurement signal in such a manner that the actual value signal approaches a predefinable target value signal over time, and
  the device control unit configured to control the target device by means of the mobile device on the basis of whether the approach has taken place.

A control loop may be used to check whether the mobile device is in the room. In this case, the mobile device with its signal receiver is part of the control loop. The signal receiver is arranged in the spatial vicinity of the mobile device in such a manner that they are in the room together or are outside the room together during normal operational use.

In a manner comparable to the target device, said signal source is designed for permanent arrangement in the room. This means, the signal source remains in the room during normal operational use. Overall, the mobile device and the signal receiver are therefore mobile and the target device and the signal source are stationary in the room. In one exemplary embodiment, the device control unit is also stationary in the room, in particular as equipment which is separate from the target device and the mobile device, or as part of the target device.

The control loop is designed in such a manner that it is possible to carry out adjustment to a predefinable target value signal. When predefining the target value signal, according to some exemplary embodiments, it may be ensured that the target value signal is above background noise present in the room. This makes it possible to ensure particularly well that it is possible to distinguish between the pilot signal or the resulting room signal and the background noise present in the room. If the amplitude of the target value signal is considerably above the amplitude of the background noise in the room, the background noise can be determined using the signal receiver, according to some exemplary embodiments, and can be subtracted from the measurement signal. A sufficiently high signal-to-noise ratio may thus be achieved.

The signal control unit is responsible for controlling the signal source in the room. At the beginning of the control loop, the signal control unit controls the signal source in such a manner that the signal source emits an initial pilot signal, in particular into the room. Since in practice there is no information regarding how the pilot signal reaches the signal receiver, whether directly, by single or multiple reflections or reflections via different surfaces, a room signal is generally referred to as part of the explanations, which room signal is substantially caused by the pilot signal and reaches the signal receiver. Background noise in the room has rather only a minimal effect. The room signal may be different at each point in the room and may even be detected differently at the same point on the basis of the orientation of the signal receiver.

The signal receiver receives the room signal and outputs a measurement signal in response to the received room signal. This measurement signal is fed back to the signal control unit. The signal control unit obtains an actual value signal from the measurement signal. If the measurement signal comprises precisely the information which is intended to be compared with the predefinable target value signal, the actual value signal may correspond to the measurement signal in the simplest case. If the measurement signal contains information which is not desired or not required for a comparison with the target value signal, the actual value signal may be obtained from the measurement signal as part of the measurement signal. For this purpose, the measurement signal can be filtered, in particular, in order to obtain the actual value signal as a result. The actual value or the actual value signal is readjusted using the target value or the target value signal.

When the actual value signal has been obtained, the signal control unit controls the signal source in such a manner that the actual value signal approaches the target value signal with the next pass of the control loop, provided that the mobile device is actually present.

One possible control loop is intended to be explained in more detail using a exemplary embodiment. For this purpose, it is assumed that the aim of the control loop is to adjust the amplitude of the actual value signal to an amplitude predefined using the target value signal. If the signal control unit determines from the actual value signal obtained from the measurement signal that the amplitude of the actual value signal is too low, the signal control unit controls the signal source in such a manner that the amplitude of the pilot signal is increased. Conversely, if the amplitude of the actual value signal is above the amplitude of the target value signal, the amplitude of the pilot signal is reduced. In this case, the amplitude may be an instantaneous amplitude or else an effective amplitude which results on temporal average from a pulsed instantaneous amplitude. According to some exemplary embodiments, the feedback loop (step response time) may be very much shorter than the periods of the signal fluctuations which are caused by the changes in the position of the mobile device (movement by the operator).

Other parameters of a signal can also be readjusted in the same manner. In other exemplary embodiments, the frequency and/or the phase is/are readjusted. If the actual value signal approaches the predefined target value signal during one or more passes of the control loop, this is considered to be an indication of the fact that the mobile device is in the same room as the stationary signal source. This in turn means that the mobile device and the stationary target device are in the same room. Control of the target device by the mobile device can therefore be allowed. In some exemplary embodiments, additional plausibility checks are carried out before a control command is transmitted from the mobile device to the target device for execution.

If, despite the described control, the actual value signal does not approach the target value signal, this is an indication of the fact that the mobile device is not in the same room as the stationary signal source. In this case, exemplary embodiments provide for the device control unit to not control the target device even if a corresponding control command is received from the mobile device.

Three exemplary variants for controlling the target device by means of the mobile device on the basis of whether the approach has taken place are as follows: a) control of the target device by the mobile device is prevented if it is not possible to determine that the actual value signal approaches the target value signal; b) control of the target device by the mobile device is allowed in principle if it is determined that the actual value signal approaches the target value signal; c) a combination of variants a) and b).

In one exemplary embodiment, the signal source is an apparatus separate from the device control unit, the mobile device and the target device. In some exemplary embodiments, the signal control unit is part of the device control unit or part of the target device.

The signal source is designed to emit different pilot signals on the basis of the control by the signal control unit. In some exemplary embodiments, the signal source is designed to change the pilot signal by means of amplitude modulation and/or pulse-width modulation. In some exemplary embodiments, the actual value signal is a numerical actual value and the target value signal is a numerical target value.

In some exemplary embodiments, the mobile device may be connected to the device control unit or, in some exemplary embodiments, to the signal control unit via a wireless connection. In this case, a connection via WLAN or via Bluetooth may be used, in particular.

In one refinement, the signal source is designed to emit an optical signal and the signal receiver is designed to receive an optical signal, the optical signal being an infrared signal, in particular.

The pilot signal may not influence the room acoustics and there may also be no need to select the amplitude of the pilot signal to be above a normal noise level in the room. In this case, the frequency or the spectrum of the optical signal, in particular, is selected in such a manner that the human visual perception in the room is influenced only minimally or, in some exemplary embodiments, not at all.

In another refinement the optical signal is an infrared signal. An infrared signal is intended to be understood as meaning, in exemplary embodiments, a signal having a wavelength of between 750 and 3000 nm, or between 760 and 1400 nm (near infrared range) or between 770 and 1200 nm. In other exemplary embodiments, a range of 800 to 1000 nm, or 850 to 985 mm or 900 to 975 nm may be chosen. Specifically, in one exemplary embodiment, a signal source having a wavelength of at least approximately 950 nm is used.

An infrared signal may be distributed well in a room and may not perceived by a user or may at least not perceived as disruptive by a user. Here, the signal source is designed to emit the pilot signal as an optical signal. The actual value signal is an infrared component of the detected room signal, in particular. If the room signal reaches the signal receiver in a form which has already been filtered to the infrared component, the measurement signal can be directly used as the actual value signal in one exemplary embodiment. With a corresponding measurement signal, the measurement signal can naturally also be directly used as the actual value signal in all other refinements. In addition, it was recognized within the scope of the disclosure that optical signals can be limited more easily than radio signals by means of structural measures.

In another refinement, the actual value signal is an infrared component of the detected room signal.

A larger wavelength range can be received using the signal receiver, but only an infrared component of the detected room signal is converted into the actual value signal which is then in turn compared with the target value signal.

In one refinement, the actual value signal is an actual value of the luminance or an actual value of the brightness or an actual value of the intensity of the detected room signal.

This refinement can be readily implemented in terms of metrology.

In another refinement, the device control unit is designed to determine whether the approach takes place within a tolerance window, the tolerance window being defined by a predefinable maximum duration for the approach and/or a predefinable maximum distance between the actual value signal and the target value signal.

This refinement effectively makes it possible to determine whether an approach has taken place, i.e., whether control of the target device is intended to be made possible in principle, or whether an approach has not taken place. If the mobile device is in the same room in which the control loop is implemented using the signal source, the actual value signal is expected to approach the target value signal. Depending on the design of the control loop, it is possible to use either theoretical considerations or empirical measurements to determine how quickly the approach takes place and/or how short the distance between the actual value signal and the target value signal becomes.

If it is determined, for example, that an approach usually takes place within 0.5 s, the tolerance window can be stipulated to be, for example, twice as large, thus 1 s. If an approach takes place in this time range of the tolerance window, this is an indication of the fact that the mobile device is in the same room. In the same manner, it is possible to check how close the actual value signal can come to the target value signal. If a predefined maximum distance between the actual value signal and the target value signal is undershot, this is an indication of the fact that the mobile device is in the same room.

In one refinement, the tolerance window is defined both with regard to the time and with regard to the maximum distance. This means that the presence of the mobile device in the same room is inferred only if the approach takes place within a particular time and undershoots a particular maximum distance in the process. In this case, the tolerance window can also be dynamically controlled, with the result that the presence of the mobile device in the same room is assumed, in particular, even in the case of a slow approach which results, however, in a particularly short distance between the actual value signal and the target value signal or in the case of a distance which is actually too large but has been reached in a particularly fast manner.

In another refinement, the apparatus is designed to change the target value signal over time.

This refinement increases the reliability when detecting the presence of the mobile device. For this purpose, the target value signal is changed at intervals of time. For the control loop, this means that the actual value signal must now be tracked to a new target value signal. If the actual value signal can no longer approach the target value signal after the target value signal has been changed, this indicates that the mobile device is not in the room or is no longer in the room. In one exemplary embodiment, a tolerance window within which the approach must take place is defined for the situation in which the actual value signal approaches the changed target value signal. For the possible configurations of the tolerance window, reference is made to the tolerance window described further above. The principle of feedback and the expected approach is therefore retained but also additionally has a signal jump which can be verified in terms of time.

In another refinement, the signal jump may produce a considerable change. A considerable change may be understood, for some exemplary embodiments, as meaning an increase of at least 10%, or at least 25%, or at least 100% or at least 250%. For some exemplary embodiments, a reduction from 100% to at most 90%, or to at most 80%, or to at most 50% or to at most 40% may likewise be understood as meaning a considerable change. In other exemplary embodiments, a considerable change may be understood as meaning an increase by a factor of at least 5, or at least 10, or at least 25 or at least 100. In other exemplary embodiments, a reduction by a factor of at most 0.2, or most 0.1, or at most 0.04 or at most 0.01 may likewise be understood as meaning a considerable change. In other exemplary embodiments, a range of 10 to 100 or 0.1 to 0.01 may be chosen.

In another refinement, the measurement signal represents a temporal sequence of the room signal received by the signal receiver.

This refinement provides extended possibilities when evaluating the measurement signal, in particular when obtaining the actual value signal from the measurement signal. If, for example, temporal changes in the measurement signal are intended to be taken into account, this can be supported by evaluating information at different times. In particular, if the measurement signal contains information relating to a time at which the signal source transmits and relating to a second time at which the signal source does not transmit, a difference analysis, here the so-called "two samples difference" in particular, can be used to separate constant components and dynamic components in the measured value signal, in particular. In one exemplary embodiment, the actual value signal contains only the dynamic components from the measurement signal, in particular those components which can change within one second, and does not contain any constant components, in particular those which do not change or change only slightly within one second.

In another refinement, the signal receiver is a camera and, in particular, the measurement signal is a temporal sequence of images which have been recorded by the camera.

This refinement makes it possible to easily record optical signals. Since a high image quality need not be paramount in the camera but rather the reception of the room signal caused by the pilot signal, cost-effective cameras can be used in exemplary embodiments. If a temporal sequence of at least two images is transmitted in the measurement signal, dynamic and constant components in the measurement signal can be easily identified, as explained above. In exemplary embodiments, the pilot signal is pulsed or its intensity is varied.

In an alternative refinement, the image data is already processed before being injected into the measurement signal, in particular by the mobile device, with the result that the measurement signal contains only the analysis data. This makes it possible to reduce the volume of data transmitted using the measurement signal. In particular, if only the overall brightness or the overall luminance or the overall intensity of the images is intended to be evaluated, according to some exemplary embodiments, these values are calculated and only these values are then injected into the measurement signal and transmitted to the signal control unit.

In another refinement, the signal source is designed to provide a desired signal strength by emitting a variable transmission power and/or by means of an accordingly pulsed constant transmission power.

This refinement makes it possible to provide the control loop with sufficient flexibility for the actual value signal to approach the target value signal. If the signal source has a variable transmission power, the transmission power can be easily increased if the actual value signal is below the target value signal and vice versa. If the signal source emits a pulsed pilot signal, the pulse length can be increased and/or the pause time between individual pulses can be reduced if the actual value signal is below the target value signal and vice versa. In some exemplary embodiments, the signal source can be changed both with regard to its transmission power (amplitude modulation) and with regard to the emitted pulses (pulse-width modulation).

In another refinement, the signal receiver is a camera installed in the mobile device, to which a filter which transmits infrared is fitted, and a wide-angle lens is additionally fitted, in particular.

This refinement can be implemented in a particularly cost-effective manner. A commercially available portable computer, in particular a tablet, can therefore be used as the mobile device for controlling target devices. Such devices generally already have an installed camera ex works. Although the image quality of these cameras is limited, it has been recognized that an installed camera is also sufficient for the purpose of detecting presence, as disclosed here.

If the optical signal is an infrared signal, the filter which transmits infrared is used to ensure that substantially only infrared components reach the camera. As a result, the normal, visible ambient light does not reach the camera or reaches the camera only in a highly attenuated form. This facilitates the evaluation of images from the camera with respect to the infrared components in the image.

If a wide-angle lens is additionally fitted in one exemplary embodiment, the dependence of the room signal received by the camera on the positioning of the mobile device in the room is reduced. In exemplary embodiments, a fish-eye lens, a 360° lens, a ball lens or a panorama lens is used here. This makes it possible to take into account an uneven characteristic of the measurement signal from a tablet camera, in particular.

In another refinement, the spatial vicinity of the signal receiver and the mobile device is configured in such a manner that the mobile device and the signal receiver are at a distance of less than 5 m, or less than 2 m, or less than 1 m or less than 0.5 m from one another. If, according to an exemplary embodiment, the mobile device has a device trolley, a camera is structurally fastened to the device trolley as the signal receiver.

This refinement can be used to ensure that the mobile device cannot be situated in a first room where a target device can be controlled and the signal receiver is situated in a second room where a different target device can be controlled. In one exemplary embodiment, the spatial vicinity of the mobile device and the signal receiver is structurally configured in such a manner that it cannot be changed by a user during the normal workflow or at least cannot be changed beyond a maximum distance. In another exemplary embodiment, the spatial vicinity is alternatively or additionally structurally configured in such a manner that the mobile device and the signal receiver cannot be separated from one another.

In another refinement, the spatial vicinity is configured in such a manner that the signal receiver is installed in the mobile device.

This makes it possible to ensure that the signal receiver cannot be separated from the mobile device, at least not during the normal workflow and not without extensive technical interventions.

In another refinement, the apparatus has an additional mobile device having an additional signal receiver for receiving the room signal, the additional signal receiver configured to output an additional measurement signal in response to the received room signal, and the device control unit also configured to control the target device by means of the additional mobile device on the basis of whether a change in the target value signal leads to a corresponding change in the additional measurement signal.

This refinement makes it possible to check the presence of further mobile devices, in particular in the room. Whereas the presence of the mobile device after a change in the target value signal is checked by determining whether the mobile device manages to bring the actual value signal closer to the target value signal again, a check is carried out for the additional mobile device in order to determine whether the change in the target value signal, which results in a change in the pilot signal and in the room signal, can also be detected in the additional measurement signal. In this case, for some exemplary embodiments, the target value signal may change considerably. The intended meaning of a considerable change has already been explained above.

The considerable change in the target value signal in comparison with the actual value signal causes a corresponding change in the pilot signal since the signal control unit attempts to readjust to the new target value signal. If the target value signal is increased considerably, for example, this also results in an increase in the pilot signal and therefore in the room signal via the control loop. If this change is also detected by the additional mobile device in a corresponding manner, possibly with a slight time delay, this is an indication of the fact that the additional mobile device is in the same room. If the additional measurement signal does not change or changes in the opposite direction, this is an indication of the fact that the additional mobile device is not in the same room.

In another refinement, a luminescent coating, a luminescent film or a luminescent element is arranged in front of the signal receiver which may be, according to some exemplary embodiments, a camera installed in the mobile device.

Light may be "volatile", meaning, the brightness signature in the room may change very quickly. The signal receiver must therefore be quick enough to follow it. According to some exemplary embodiments, this dynamic response may be attenuated or smoothed from the point of view of the signal receiver. In the further refinement, luminescent or "light-storing" coatings, films or elements are used for this purpose. This makes it possible to attenuate the brightness changes for the signal receiver. It could operate more slowly, in particular could record fewer images per second, and could therefore be less powerful.

According to another aspect, the object is achieved by means of a method for detecting the presence of a mobile device in a room, the method having the steps of:

controlling a signal source for the purpose of emitting a pilot signal, receiving a room signal caused by the pilot signal, outputting a measurement signal on the basis of the room signal received by a mobile device, obtaining an actual value signal from the measurement signal, comparing the actual value signal with a predefinable target value signal, adapting the control of the signal source, with the result that the actual value signal approaches a predefinable target value signal over time, controlling the target device by means of the mobile device on the basis of whether the approach has taken place.

In one refinement, the method also has the following steps of:

outputting an additional measurement signal on the basis of the room signal received by an additional mobile device, changing the target value signal, controlling the target device or an additional target device by means of the additional mobile device on the basis of whether the changing of the target value signal results in a corresponding change in the additional measurement signal.

According to another aspect, the object is achieved by means of a medical treatment room in which an apparatus for detecting presence (described above) is arranged and wherein at least the device control unit, the signal source, the signal control unit and the target device are situated in the medical treatment room, in particular in a stationary manner.

In this case, according to exemplary embodiments, the two medical treatment rooms may have different target value signals and that, in the event of a change in a target value signal in one treatment room, the change is made to a target value signal which is different, according to some exemplary embodiments considerably different, from the target value signal in the other treatment room.

It goes without saying that the features mentioned above and the features yet to be explained below can be used not only in the respectively stated combination but also in other combinations or alone without departing from the scope and spirit of the present disclosure.

BRIEF DESCRIPTION OF THE DRAWINGS

Exemplary embodiments are illustrated in more detail in the drawing and are explained in more detail in the following description. In the drawing.

DESCRIPTION OF EXEMPLARY EMBODIMENTS

Figure 1:
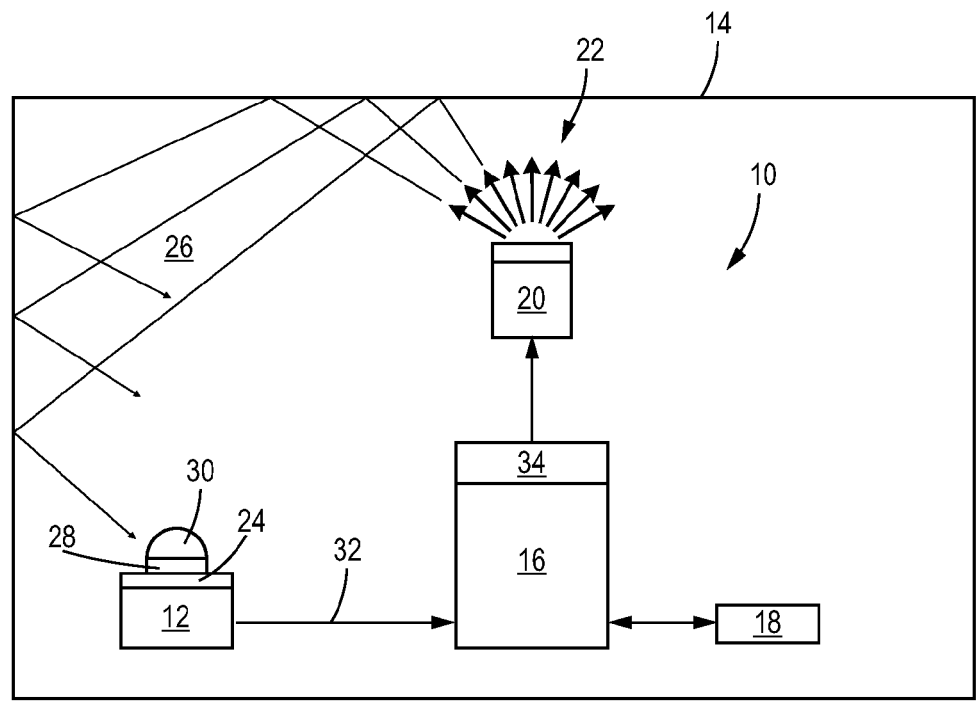
FIG. 1 shows a first embodiment of an apparatus for detecting presence.

FIG. 1 shows an apparatus 10 for detecting the presence of a mobile device 12 in a room 14. The apparatus 10 has a device control unit 16 for controlling a target device 18. The mobile device 12 is designed to control the target device 18 using the device control unit 16.

The apparatus 10 also has a signal source 20 for emitting a pilot signal 22, the pilot signal 22 being symbolically represented here by means of a plurality of arrows. The apparatus also has a signal receiver 24 which is designed to receive a room signal 26 caused by the pilot signal 22. The room signal 26 is symbolized here by means of long thin arrows and substantially pervades the entire room 14, the room signal 26 being position-variant, i.e., the room signal 26 is also different at different points in the room 14.

The signal receiver 24 is arranged in the spatial vicinity of the mobile device 12, the signal receiver 24 here being a camera which is installed in the mobile device 12. A filter 28 which transmits infrared is fitted to the signal receiver 24 here. A wide-angle lens 30 is additionally fitted to the filter 28. The signal receiver 24 is designed to output a measurement signal 32 in response to the received room signal 26.

The apparatus 10 also has a signal control unit 34 which is designed to control the signal source 20. The signal control unit 34 is also designed to control the signal source 20 on the basis of an actual value signal 36 (see FIG. 7) obtained from the measurement signal 32 in such a manner that the actual value signal 36 approaches a predefinable target value signal 38 (see FIG. 7) over time t (see FIG. 7). The device control unit 16 is designed to control the target device 18 by means of the mobile device 12 on the basis of whether the approach has taken place.

The signal source 20 is designed to emit the pilot signal 22 as an optical signal. The signal receiver 24 is designed to receive the room signal 26 as an optical signal. In this case, the optical signal is an infrared signal, in particular. The actual value signal 36 is an infrared component of the detected room signal 26, in particular. If the room signal 26 reaches the signal receiver 24 in a form already filtered to the infrared component, the measurement signal 32 can be directly used as the actual value signal 36 in one exemplary embodiment.

In this case, the actual value signal 36 is an actual value of the intensity of the detected room signal 26. In other exemplary embodiments, the actual value signal 36 is an actual value of the luminance or an actual value of the brightness of the detected room signal 26. The device control unit 16 is designed to determine whether the approach takes place within a tolerance window 40 (see FIG. 7), the tolerance window 40 being defined by a predefinable maximum duration T (see FIG. 7) for the approach and/or a predefinable maximum distance D (see FIG. 7) between the actual value signal 36 and the target value signal 38.

The apparatus 10 is designed to change the target value signal 38 over time t. In the embodiment shown here, the device control unit 16 is designed, in particular, to change the target value signal 38 over time t. The measurement signal 32 may represent a temporal sequence of the room signal 26 received by the signal receiver 24. In the case shown here in which the signal receiver 24 is a camera, the measurement signal 32 is a temporal sequence of images which have been recorded by the camera.

The signal source 20 is designed to provide a desired signal strength by means of an accordingly pulsed constant transmission power. Depending on the length of the pulse of the constant transmission power and the length of the pause during which the signal source 20 does not transmit, the result is an effective transmission power which can be varied. In other embodiments, the signal source 20 has a variable transmission power, the signal source 20 then also being able to transmit without a pause. In further exemplary embodiments, both possibilities of varying the desired signal strength are combined.

Figure 2:
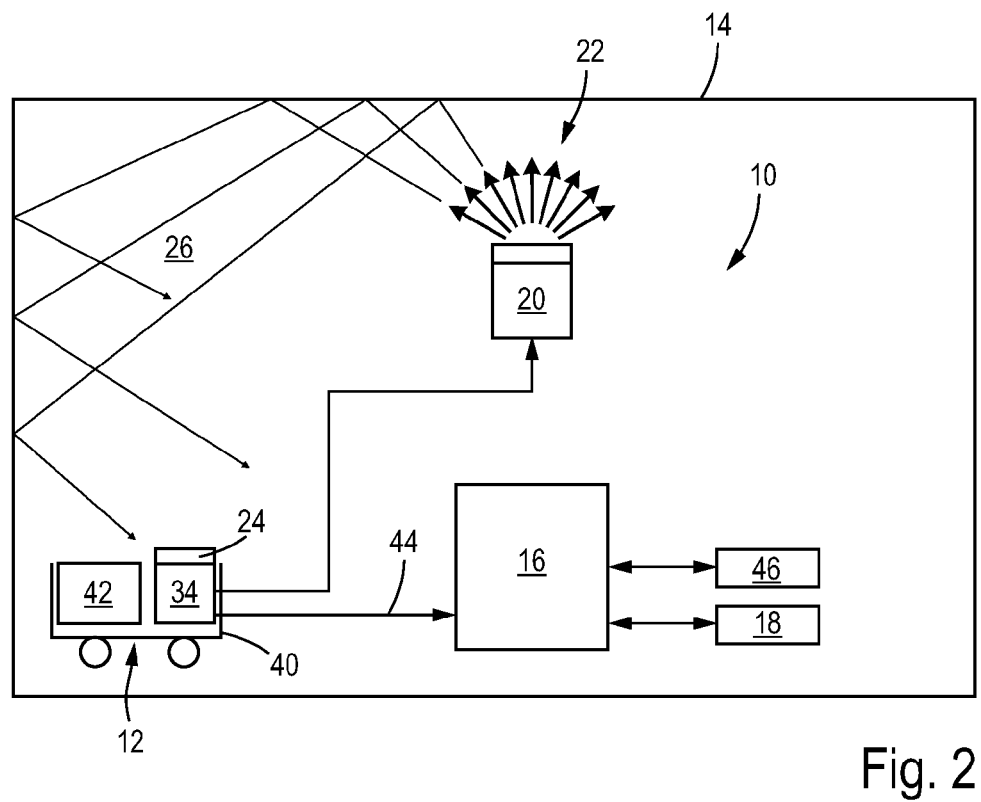
FIG. 2 shows a second embodiment of an apparatus for detecting presence.

FIG. 2 shows a second embodiment of an apparatus 10 for detecting presence. All statements which have been made in connection with FIG. 1 apply here. In addition, the reference symbols which have already been introduced continue to be used here and below and indicate identical or functionally identical elements. In contrast to FIG. 1, the mobile device 12 here is a combination of a trolley 40 and a device 42 positioned on the trolley 40. The signal receiver 24 is arranged on the trolley 40 here, but the fastening of the device 42 ensures that the signal receiver 24 cannot be separated from the mobile device 12, i.e., neither from the trolley 40 nor from the device 42. In addition, the signal control unit 34 is embodied together with the signal receiver 24 here. Since the measurement signal 32 does not leave the assembly of the signal receiver 24 and the signal control unit 34 in this refinement, the measurement signal 32 is not illustrated here.

If the control loop via the signal source 20 results in an approach, an enable signal 44 is transmitted, which signal makes it possible for the mobile device 12 to control the target device 18. Finally, an additional target device 46 is also present in the second embodiment and can be controlled simultaneously or alternatively from the mobile device 12.

Figure 3:
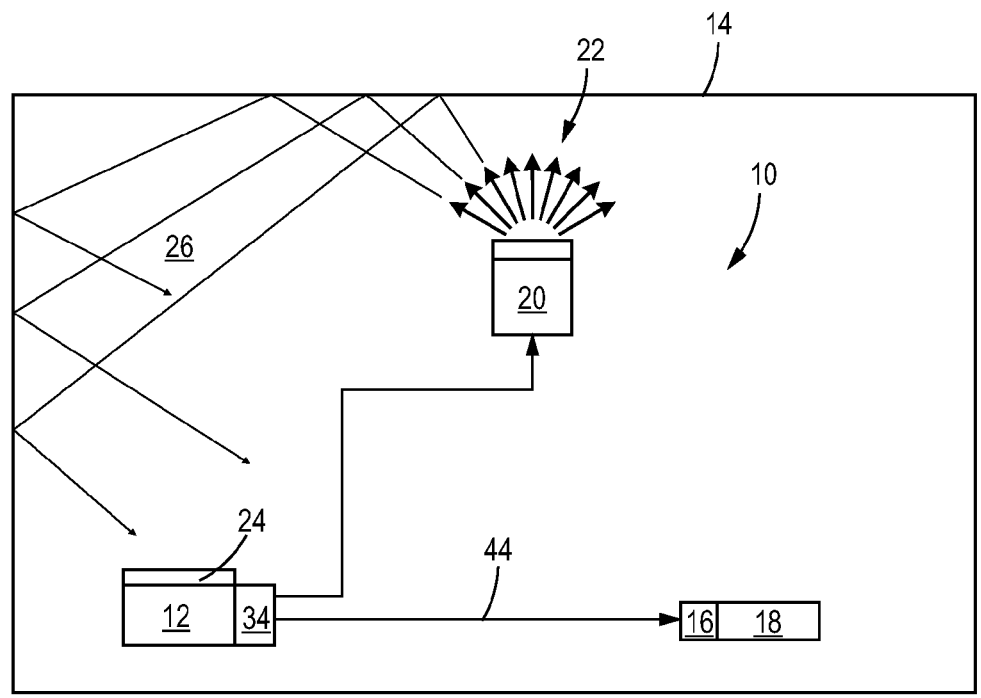
FIG. 3 shows a third embodiment of an apparatus for detecting presence.

FIG. 3 shows a third embodiment of an apparatus 10 for detecting presence. The statements made with respect to the individual elements in connection with FIG. 1 apply here. In this refinement, the device control unit 16 is integrated in the target device 18. If the control loop via the signal source 20 results in an approach, an enable signal 44 is transmitted, which signal makes it possible for the mobile device 12 to control the target device 18. In this case, the signal control unit 34 is part of the mobile device 12.

Figure 4:
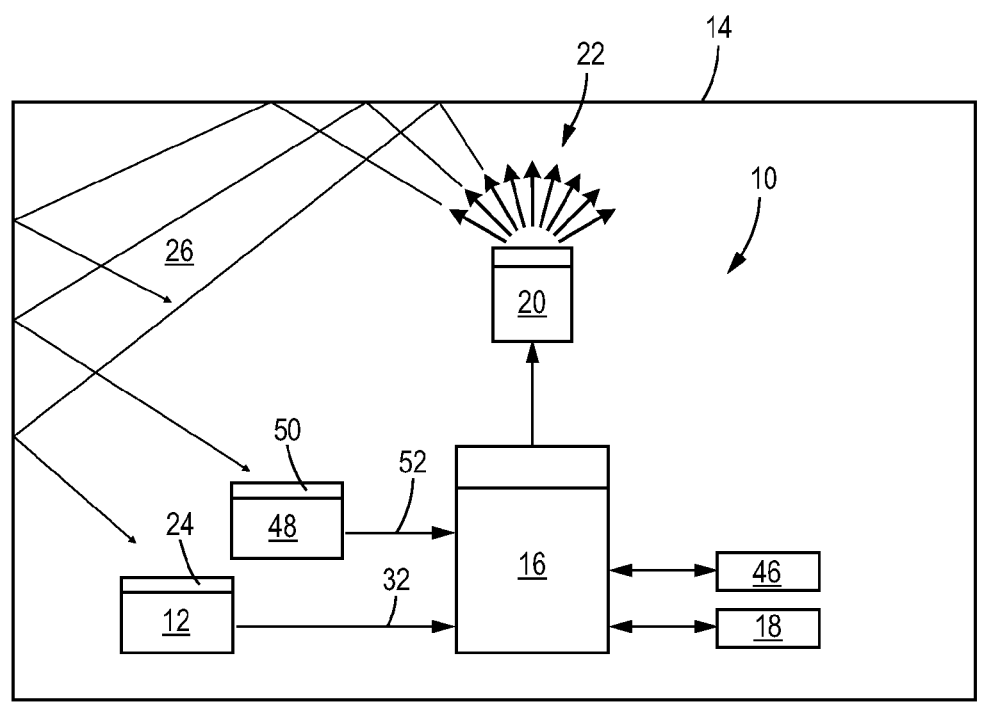
FIG. 4 shows a fourth embodiment of an apparatus for detecting presence.

FIG. 4 shows a fourth embodiment of an apparatus 10 for detecting presence. The statements made with respect to the individual elements in connection with FIG. 1 and FIG. 2 apply here. The apparatus 10 also has an additional mobile device 48 with an additional signal receiver 50 for receiving the room signal 26. The additional signal receiver 50 is designed to output an additional measurement signal 52 in response to the received room signal 26. In this case, the device control unit 16 is also designed to control the target device 18 or the additional target device 46 by means of the additional mobile device 48 on the basis of whether a change in the target value signal 38 results in a corresponding change in the additional measurement signal 52. This also makes it possible to detect the presence of any desired number of further additional devices.

Figure 5:
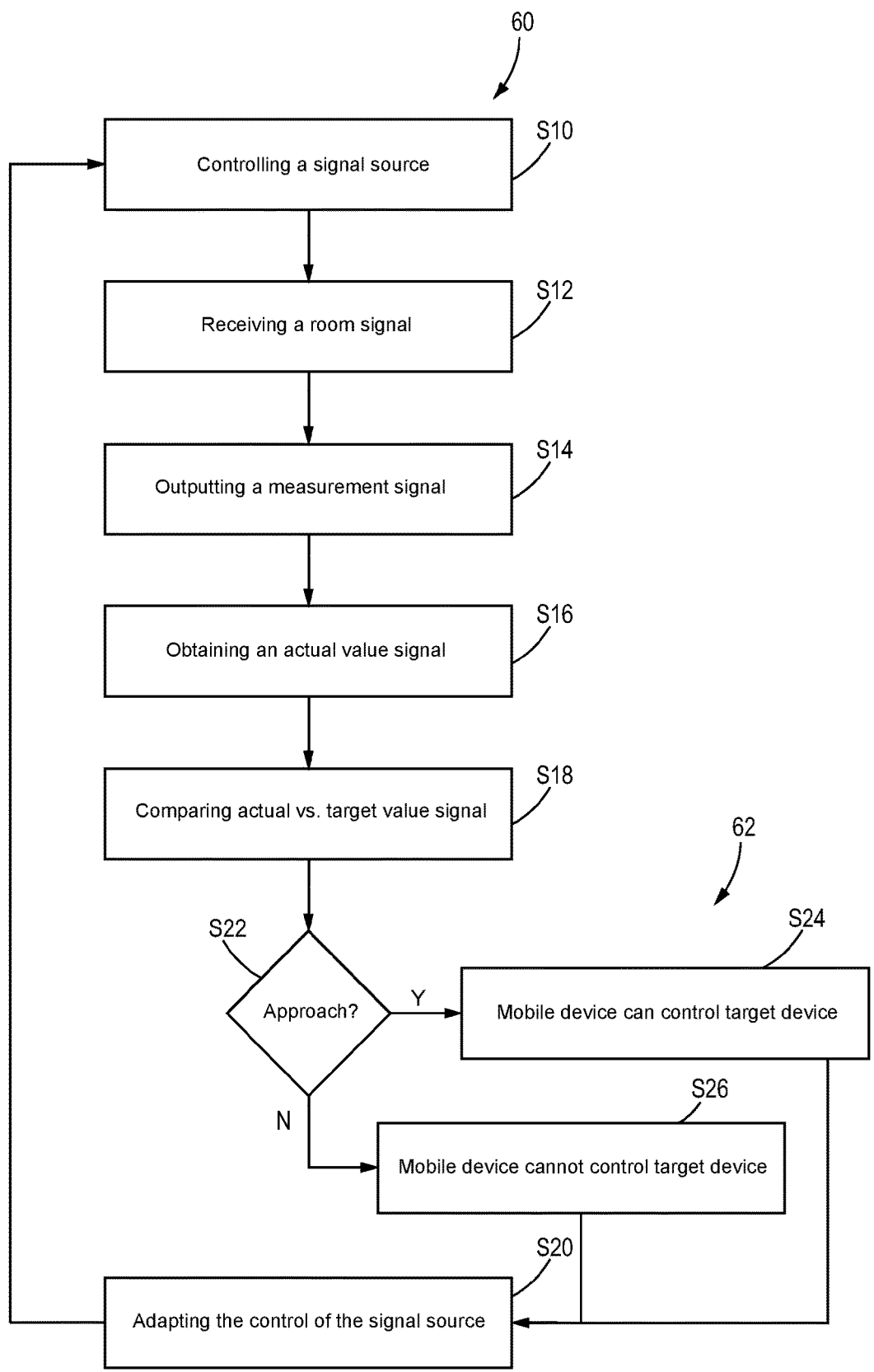
FIG. 5 shows a first embodiment of a method for detecting presence.

FIG. 5 shows a first exemplary embodiment of a method 60 for detecting the presence of a mobile device 12 in a room 14. The method 60 first of all has step S10 in which a signal source 20 is controlled for the purpose of emitting a pilot signal 22. In step S12, a room signal 26 caused by the pilot signal 22 is received. A measurement signal 32 is output in step S14 on the basis of the room signal 26 received by the mobile device 12. In step S16, an actual value signal 36 is obtained from the measurement signal 26.

The actual value signal 36 is compared with a predefinable target value signal 38 in step S18. In a step S20, the control of the signal source 20 is adapted such that the actual value signal 36 approaches the predefinable target value signal 38 over time.

In a block 62, the target device 18 is controlled by the mobile device 12 on the basis of whether the approach has taken place. In this case, it is first of all determined in a comparison step S22 whether the approach has taken place, also see the explanation in FIG. 7 below in this respect. If this is the case, the method branches, via the branch Y, to step S24 in which it is possible for the mobile device 12, in particular by means of an enable signal 44, to control the target device 18. If an approach has not taken place, the method branches, via the branch N, to step S26 where the mobile device 12 is prevented from controlling the target device 16.

After the control of the signal source has been adapted in step S20, the method is continued with step S10, i.e., the signal source 20 transmits an adapted pilot signal 22.

Figure 6:
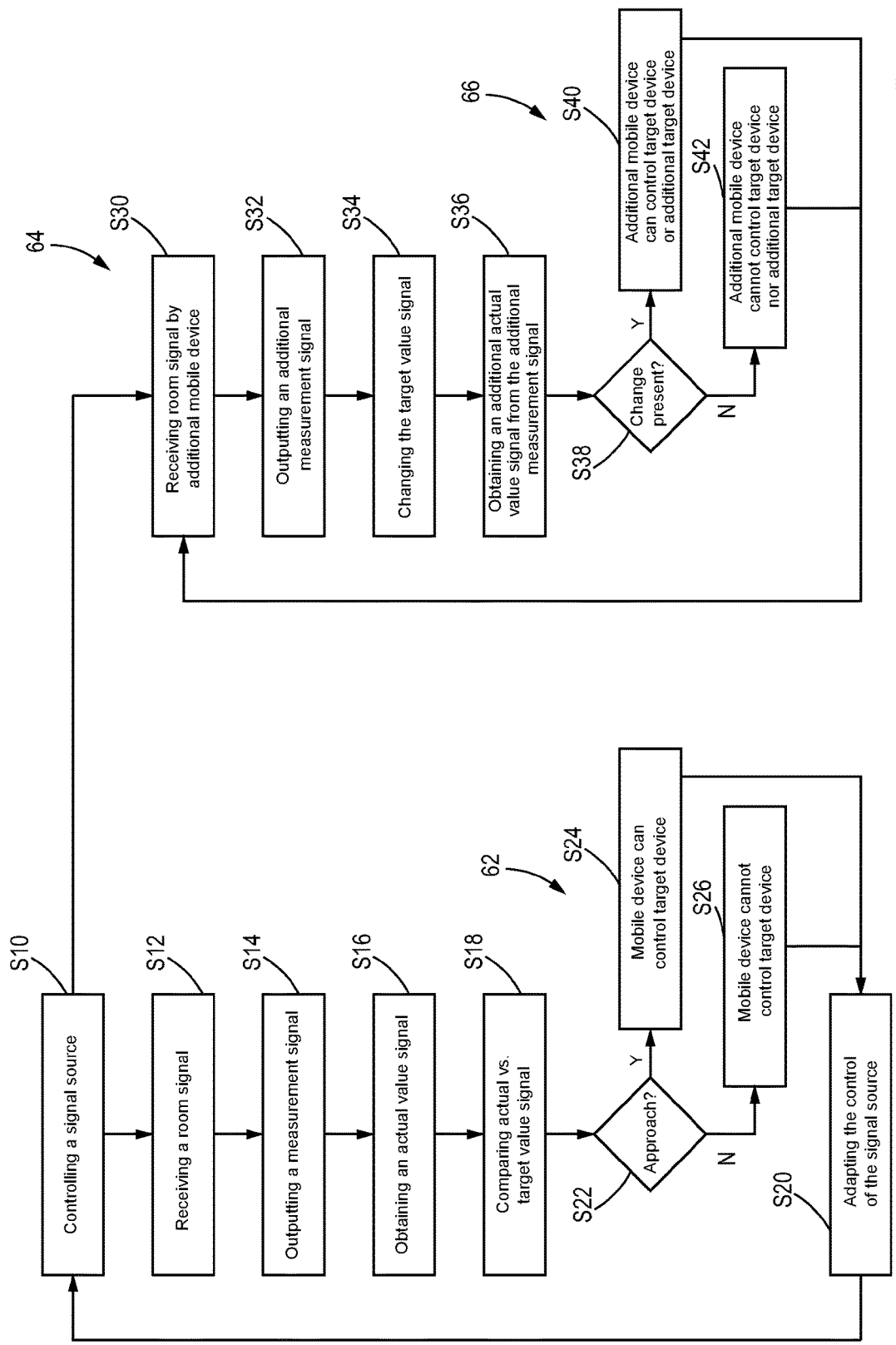
FIG. 6 shows a second embodiment of a method for detecting presence.

FIG. 6 shows a second embodiment of a method 64 for detecting presence. The left-hand part of the illustration corresponds to the illustration from FIG. 5. All of the explanations made in the context of FIG. 5 therefore also apply here.

In addition to FIG. 5, the room signal 26 caused by the pilot signal 22 is now also received by an additional signal receiver 50 of an additional mobile device 48 here in step S30. Since the additional signal receiver 50 cannot be situated at the same position as the signal receiver 24 and also probably does not have the same orientation in the room 14, the signal receiver 24 and the additional signal receiver 50 do not receive an identical room signal 26.

In step S32, an additional measurement signal is output on the basis of the room signal 26 received by the additional mobile device 48. In step S34, the target value signal 38 is changed. However, the target value signal 38 can also be changed at another time, in which case the change can be carried out, in particular, independently of the method step in which the method 60, 64 is situated. Step S34 has been arranged after step S32 only for this exemplary embodiment.

In the optional step S36, an additional actual value signal is obtained from the additional measurement signal 52. This step may be carried out if the subsequent control 66 of the target device 18 can be simplified thereby. In this case, the target device 18 is then controlled on the basis of whether the change in the target value signal 38 results in a corresponding change in the additional actual value signal. The check in order to determine whether a corresponding change takes place, may be carried out with a time delay in order to provide the control system with some time to detect the change.

In a block 66, the target device 18 or the additional target device 46 is controlled by means of the additional mobile device 48 on the basis of whether the changing of the target value signal 38 results or has resulted in a corresponding change in the additional measurement signal 52. In this case, it is first of all determined in a comparison step S38 whether the corresponding change is present. If this is the case, the method branches, via the branch Y, to step S40 in which it is possible for the additional mobile device 48, in particular by means of an enable signal, to control the target device 18 or the additional target device 46. If no corresponding change is present, the method branches, via the branch N, to step S42 where the additional mobile device 48 is prevented from controlling the target device 18 or the additional target device 46.

In this refinement, the presence of the mobile device 12 is detected by virtue of the fact that the actual value signal 36—which corresponds to the measurement signal 26 in exemplary embodiments—can be tracked to the target value signal 38. The presence of the additional mobile device 48 or further mobile devices is checked by determining whether a change in the target value signal 38 can also be detected by the additional signal receiver 50 in the additional mobile device 48.

Figure 7:
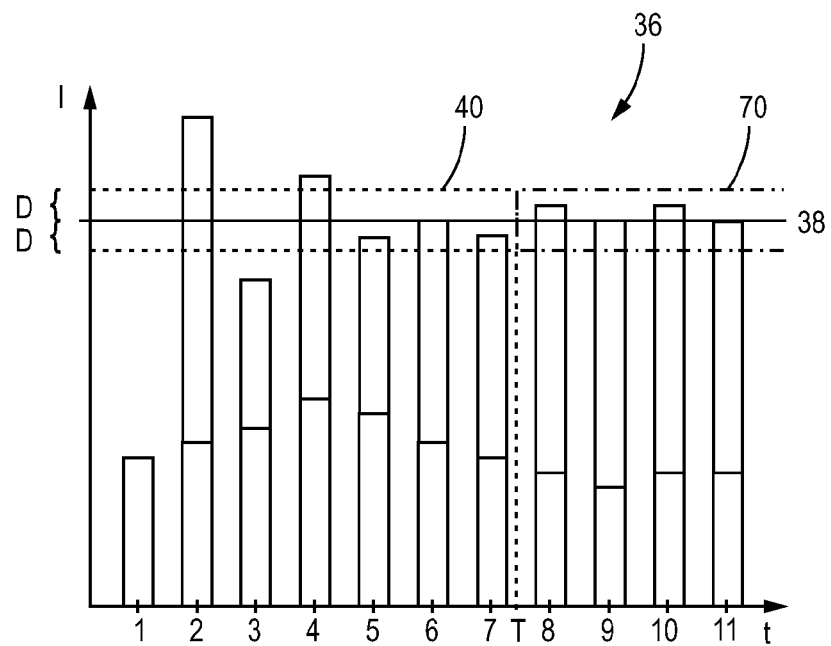
FIG. 7 shows an exemplary embodiment of a temporal profile when an approach takes place.

FIG. 7 shows a first exemplary profile of the actual value signal 36. In this case, the time t is plotted along the x axis and the intensity I is plotted along the y axis. The background intensity or the background noise in the room is respectively plotted in a lower part of the bar, which background noise can change, for example, as a result of incident daylight, movable luminaires in the room or as a result of changes in the position and orientation of the signal receiver 24. The signal source 20 is still switched off at the time t=1, with the result that only the background intensity is measured.

The signal source 20 was switched on at the time t=2, with the result that an additional component is added to the background intensity. As shown here, this addition results, however, in the target value 38 being considerably exceeded, with the result that the signal source 20 is controlled for a lower emission in a next step. In this case, the aim is to adjust the actual value signal within the tolerance window 40.

After the actual value 36 is below the tolerance window 40 at the time t=3 and is above the tolerance window 40 at the time t=4, the actual value signal 36 is within the tolerance window 40 at the times t=5, t=6 and t=7. The actual value signal 36 has therefore approached the target value 38 within the distance D and within the maximum time T. The distance D is twice in the figure in order to take into account a deviation in the positive direction by the distance D and a deviation in the negative direction by the distance D. Optionally, it is then possible to check in a further tolerance window 70 whether the approach remains.

Figure 8:
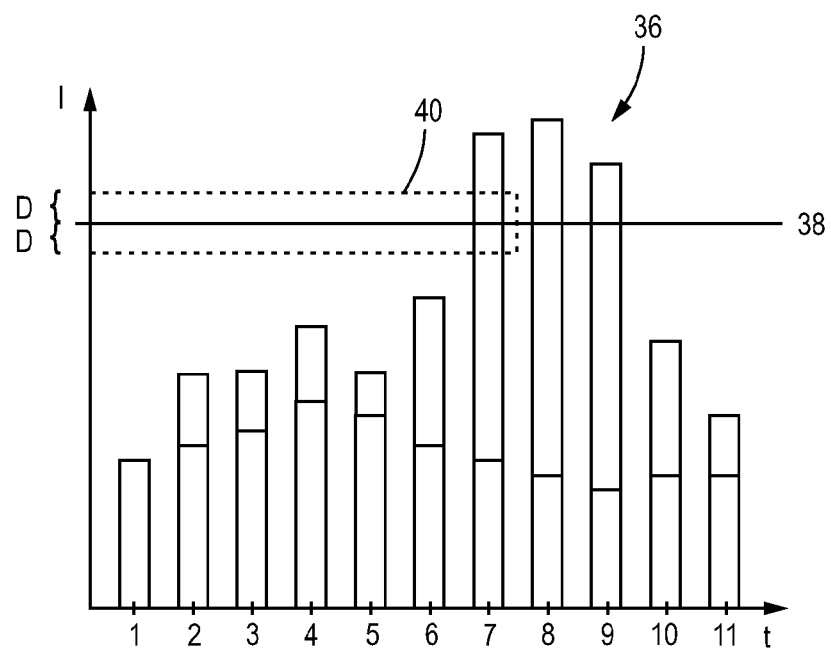
FIG. 8 shows an exemplary embodiment of a temporal profile when an approach does not take place.

FIG. 8 shows a second example of a profile of the actual value signal 36. It can be seen that the actual value signal 36 cannot be brought closer to the target value signal 38. This allows the conclusion that the mobile device 12 is not in the room 14.

Figure 9:
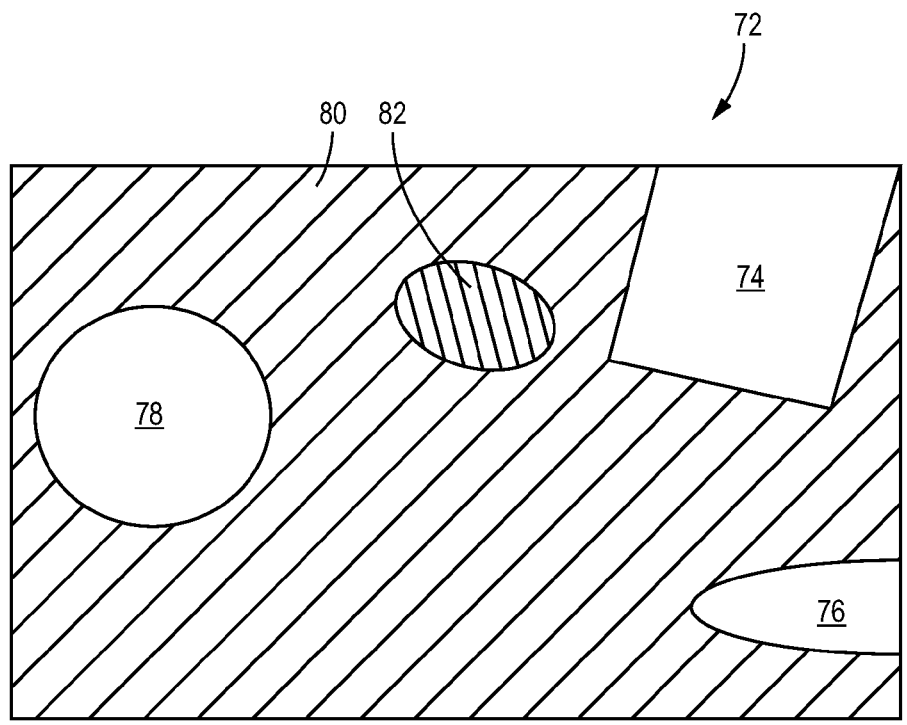
FIG. 9 shows a first image from an exemplary measurement signal.

FIG. 9 shows an exemplary embodiment of an image 72 comprising a temporal sequence of images. The sequence of images is obtained using a signal receiver 24 in the form of a camera and is transmitted in the measurement signal 32. In this case, the image 72 shows a first region 74, a second region 76 and a third region 78 each indicating a high intensity. There is also a large fourth region 80 with a medium intensity and a fifth region 82 with a low intensity. The image 72 was captured in a room 14 in which a pulsed signal source 20, i.e., a pulse-width-modulated signal source 20, is used.

Figure 10:
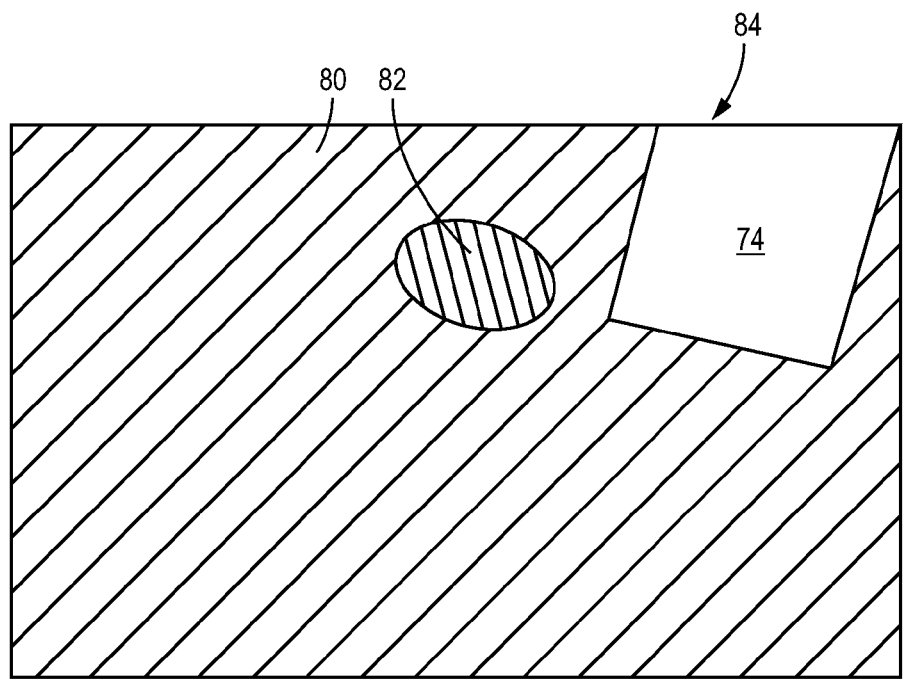
FIG. 10 shows a second image from the exemplary measurement signal.

FIG. 10 shows a second image 84 comprising an exemplary temporal sequence of images. In comparison with the image shown in FIG. 9, the second region 76 and the third region 78 are missing here. Since the individual images are recorded by the camera with a short temporal interval, the changes between the image 72 from FIG. 9 and the image 84 from FIG. 10 indicate a fast change. In exemplary embodiments, the individual images are obtained with a temporal interval of less than 500 ms, or may be less than 200 ms, or may be less than 100 ms or may be less than 50 ms.

On the basis of an analysis of the differences between the images 72, 84 from FIG. 9 and FIG. 10, it can be concluded that the second region 76 and the third region 78 are caused by the pilot signal 22. When evaluating the image according to FIG. 9, the other stationary image regions—the first region 74, the fourth region 80 and the fifth region 82—can be subtracted. On the basis of the difference analysis, only the dynamically variable regions 76, 78 are obtained and it is may be possible to concentrate on those regions of the image which are particularly brightened by the pilot signal 22 when determining the actual value signal 36.

In one exemplary embodiment, a plurality of images are analysed in this manner in order to be able to determine the intensity caused by the signal source 20. The more images exhibit the dynamic regions 76, 78 in relation to the total number of analysed images, the greater the intensity caused by the signal source 20. In exemplary embodiments, the actual value signal 36 can be determined in this manner in order to be able to correct the control of the signal source 20 with regard to the target value signal 38 to be achieved.

What is claimed is:

1. An apparatus for detecting the presence of a mobile device in a room, the apparatus comprising:
    a device control unit configured to control a target device;
    a mobile device configured to control a target device using the device control unit;
    a signal source configured to emit a pilot signal;
    a signal receiver configured to receive a room signal caused by the pilot signal, the signal receiver being arranged in a spatial vicinity of the mobile device and configured to output a measurement signal in response to the room signal received by the signal receiver;
    a signal control unit configured to control the signal source;
    the signal control unit configured to control the signal source on the basis of an actual value signal obtained from the measurement signal in such a manner that an approach of the actual value signal towards a predefinable target value signal over time is achieved when the mobile device and the signal source are both present in the room; and
    the device control unit configured to control the target device by the mobile device on the basis of whether the approach has taken place;
    wherein the room signal includes at least one of (i) the pilot signal; and (ii) the pilot signal after reflecting from one or more surfaces in the room.

2. The apparatus of claim 1, wherein the signal source is configured to emit an optical signal and the signal receiver is configured to receive an optical signal.

3. The apparatus of claim 2; wherein the optical signal is an infrared signal.

4. The apparatus of claim 1, wherein the actual value signal is an infrared component of the room signal received by the signal receiver.

5. The apparatus of claim 1, wherein the actual value signal is an actual value of a luminance or an actual value of a brightness or an actual value of an intensity of the room signal received by the signal receiver.

6. The apparatus of to claim 1, wherein the device control unit is configured to determine whether the approach takes place within a tolerance window, the tolerance window being defined by a predefinable maximum duration for the approach and/or a predefinable maximum distance between the actual value signal and the target value signal.

7. The apparatus of claim 1, wherein the apparatus is configured to change the target value signal over time.

8. The apparatus of claim 1, wherein the measurement signal represents a temporal sequence of the room signal received by the signal receiver.

9. The apparatus of claim 1, wherein the signal receiver is a camera.

10. The apparatus of claim 9, wherein the measurement signal is a temporal sequence of images which have been recorded by the camera.

11. The apparatus of claim 1, wherein the signal source configured to provide a desired signal strength by emitting a variable transmission power and/or by an accordingly pulsed constant transmission power.

12. The apparatus of claim 1, wherein the signal receiver being a camera installed in the mobile device, to which a filter which transmits infrared is fitted.

13. The apparatus of claim 12, wherein a wide-angle lens is fitted to the camera.

14. The apparatus of claim 1, the spatial vicinity being configured in such a manner that the mobile device and the signal receiver are at a distance of less than 5 m.

15. The apparatus of claim 1, the spatial vicinity being configured in such a manner that the mobile device and the signal receiver are at a distance of less than 2 m.

16. The apparatus of claim 1, the spatial vicinity being configured in such a manner that the signal receiver is installed in the mobile device.

17. The apparatus of claim 1, the apparatus having an additional mobile device having an additional signal receiver configured to receive the room signal, the additional signal receiver configured to output an additional measurement signal in response to the room signal received by the additional signal receiver, and the device control unit also configured to control the target device or an additional target device by the additional mobile device on the basis of whether a change in the target value signal leads to a corresponding change in the additional measurement signal.

18. A method for detecting the presence of a mobile device in a room, the method comprising the steps of:
controlling a signal source for the purpose of emitting a pilot signal;
receiving a room signal caused by the pilot signal;
outputting a measurement signal on the basis of the room signal received by the mobile device;
obtaining an actual value signal from the measurement signal;
comparing the actual value signal with a predefinable target value signal;
adapting the control of the signal source in such a manner that an approach of the actual value signal towards a predefinable target value signal over time is achieved when the mobile device and the signal source are both present in the room; and
controlling a target device by the mobile device on the basis of whether the approach has taken place;
wherein the room signal includes at least one of (i) the pilot signal; and (ii) the pilot signal after reflecting from one or more surfaces in the room.

19. The method of claim 18, further comprising the steps of:
outputting an additional measurement signal on the basis of the room signal received by an additional mobile device;
changing the target value signal; and
controlling the target device or an additional target device by the additional mobile device on the basis of whether the changing of the target value signal results in a corresponding change in the additional measurement signal.

* * * * *